United States Patent [19]

Nonomura

[11] Patent Number: 5,401,170
[45] Date of Patent: Mar. 28, 1995

[54] MEASURING DEVICE AND MEASURING METHOD OF IMPLANT STRUCTURE

[75] Inventor: Yuusuke Nonomura, Nagoya, Japan

[73] Assignee: Kabushiki Kaisha Egawa, Nagoya, Japan

[21] Appl. No.: 156,908

[22] Filed: Nov. 24, 1993

[30] Foreign Application Priority Data

Nov. 25, 1992 [JP] Japan .................. 4-314565

[51] Int. Cl.⁶ ............. A61C 8/00; A61C 19/04; A61C 5/00; A61C 5/10
[52] U.S. Cl. ..................... 433/173; 433/68; 433/215; 433/223
[58] Field of Search ............ 433/29, 68, 72, 172, 433/173, 174, 215, 223, 229; 33/512, 513, 514

[56] References Cited

U.S. PATENT DOCUMENTS

| | | | |
|---|---|---|---|
| 4,575,805 | 3/1986 | Moermann et al. | 433/68 X |
| 5,078,599 | 1/1992 | Eenboom et al. | 433/29 |
| 5,257,184 | 10/1993 | Mushabac | 433/72 X |
| 5,278,756 | 1/1994 | Lemchen et al. | 433/68 X |

OTHER PUBLICATIONS

Siemens, "CEREC® Computerized Ceramic Reconstruction," Intensive Course Schedule.
"From The Known To The New: Taking Control Of Restoration Quality In Your Own Office. Today." Brochure, Sopha Bioconcept Inc.
CEREC Veneers, Patient Information Brochure.
"New Technology and Trends, Expanding Dental Practice With Computer Technology," Princeton Dental Resource Center Brochure, pp. 33–36.

*Primary Examiner*—Nicholas D. Lucchesi
*Attorney, Agent, or Firm*—Sughrue, Mion, Zinn, Macpeak & Seas

[57] ABSTRACT

In a measuring technique used to restore a tooth with an employment of an implant structure, it is desirable to precisely determine the direction and position of bonding points in which a prosthesis is attached to the implant structure at the time of curing the tooth by of the implant structure. Upon precisely measuring the direction and position of bonding points in which a prosthesis is attached to the implant structure, measurement points are provided with the bonding points, and are taken a picture by a camera. In the picture thus taken, shape and position of the measurement points are measured by an image processor device by way of illustration so as to measure the positional relationship of the bonding points of the implant structure which is embedded in a human jaw.

16 Claims, 4 Drawing Sheets

MEASURING DEVICE AND MEASURING METHOD OF IMPLANT STRUCTURE

BACKGROUND OF THE INVENTION

1. Field of the Invention

This invention relates to a measuring device and measuring method for an implant structure used when a tooth is cured by using an implant structure at the time of a dental therapy.

2. Description of Prior Art

In a tooth restoration technique, there has been provided an implant structure which is embedded in the upper jaw or lower jaw of a patient. A prosthesis (brace or bridge teeth) is attached to the implant structure which has a plurality of artificial teeth. In this restoration technique, it is necessary to fix the prosthesis in a patient's mouth with high stability. For this reason, bonding portions (female thread or stud) are provided in the implant structure in order to secure the prosthesis to the implant structure by way of receiving portions (screw hole or recess) which are provided on the prosthesis. It is necessary to positionally and directionally align the bonding portions to the respective receiving portions. When the bonding portions do not correspond to the respective receiving portions, the human jaw is subjected to unfavorable strain which may lead to inflammation due to the stress applied to the implant structure. More precisely, in the case when a plurality of implant structures are implanted in the jaw, and the bonding portions do not correspond to the receiving portions, osteo-adsorption occurs in the jaw bone to cause inflammation between the implant structure and the jaw bone due to the strain applied to the implant structure. In the prior art method which specifies the positional relationship between the bonding portions and the receiving portions, an impression is used to make a mold of the patient's mouth. Wax is then poured into the mold to produce a mock which forms an upper structure of the prosthesis which contains information about the bonding portions. On the basis of the information, the receiving portions are provided with the upper structure.

However, it is difficult to precisely correspond the bonding portions to the receiving portions due to manufacturing errors resulting from numerous step molds, mold deformation and shrinkage under the influence of high temperature and used material. This is one of the important points which is to be overcome in the field of dental technique.

Therefore, it is one of the objects of the present invention to provide a measuring device and measuring method for an implant structure which is capable of precisely and quickly measuring the position and direction in which a prosthesis is attached to an implant structure.

SUMMARY OF THE INVENTION

According to the present invention, there is provided a measuring method for precisely and quickly measuring the position and direction in which a prosthesis is attached to an implant structure. The measuring method includes the steps of concurrently photographing specified shapes of measuring objects each provided on bonding portions of an implant structure embedded in a human jaw by means of a camera; measuring the shapes and determining a positional relationship of the measuring objects photographed by the camera. On the basis of the shapes of the measuring objects photographed by the camera, each direction of the bonding portions is determined. On the basis of the positional relationship of the measuring objects photographed by the camera, the positional relationship of the bonding portions is measured.

According to the invention, there is also provided a measuring device for precisely and quickly measuring the position and direction in which a prosthesis is attached to an implant structure. The measuring device includes a camera which concurrently photographs specified shapes of measuring objects each provided on bonding portions of an implant structure embedded in a human jaw; a read-out device which reads the shapes and a positional relationship of the measuring objects photographed by the camera; a calculator device which measures directions of the measuring objects on the basis of the shapes read by the read-out device while measuring a positional relationship of the bonding portions on the basis of the positional relationship of the measuring objects read by the read-out device. By measuring each of the measuring objects of the implant structure, the positions of the bonding portions of the implant structure are easily and quickly measured with high precision. With the precisely measured positions of the bonding portions, it is possible to precisely bond the prosthesis to the implant structure. This makes it possible to protect the implant structure against the unfavorable strain to avoid inflammation in the human jaw. This also makes it possible to eliminate the necessity of providing a clearance play between the prosthesis and the implant structure so as to avoid foreign matters (fouling and germs) from being caught up between the prosthesis and the implant structure.

As opposed to the prior art in which numerous steps, intensive labor and a skilled technician are required when positioning the prosthesis and the implant structure, the position of the implant structure is readily and quickly measured so as to cut the cost necessary to cure the tooth by using the implant structure.

These and other objects and advantages of the invention will be apparent upon reference to the following specification, attendant claims and drawings.

DETAILED DESCRIPTION OF THE PREFERRED EMBODIMENTS OF THE INVENTION

Figure 1:
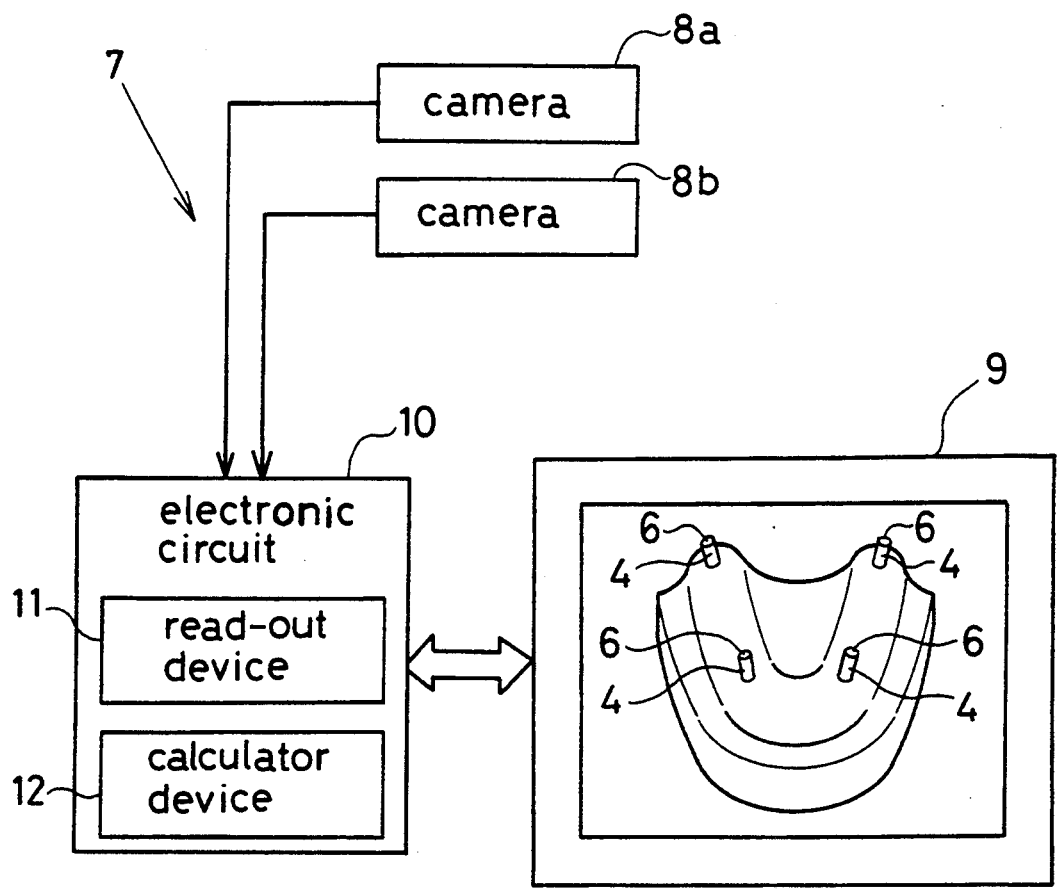
FIG. 1 is a schematic view of a block diagram of a measurement device of an implant structure according to a first embodiment of the invention.
Figure 2:
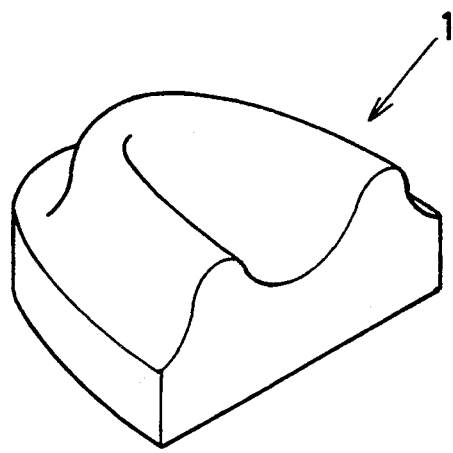
FIG. 2 is an explanatory view of a human jaw in which no tooth is depicted according to the first embodiment of the invention.
Figure 3:
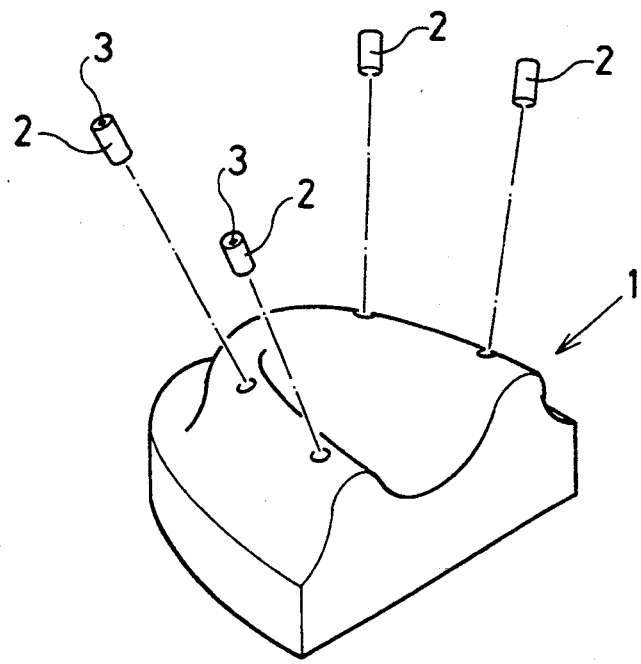
FIG. 3 is an explanatory view of the implant structure which is implanted in a human jaw at the time of carrying out a dental therapy according to the first embodiment of the invention.
Figure 4:
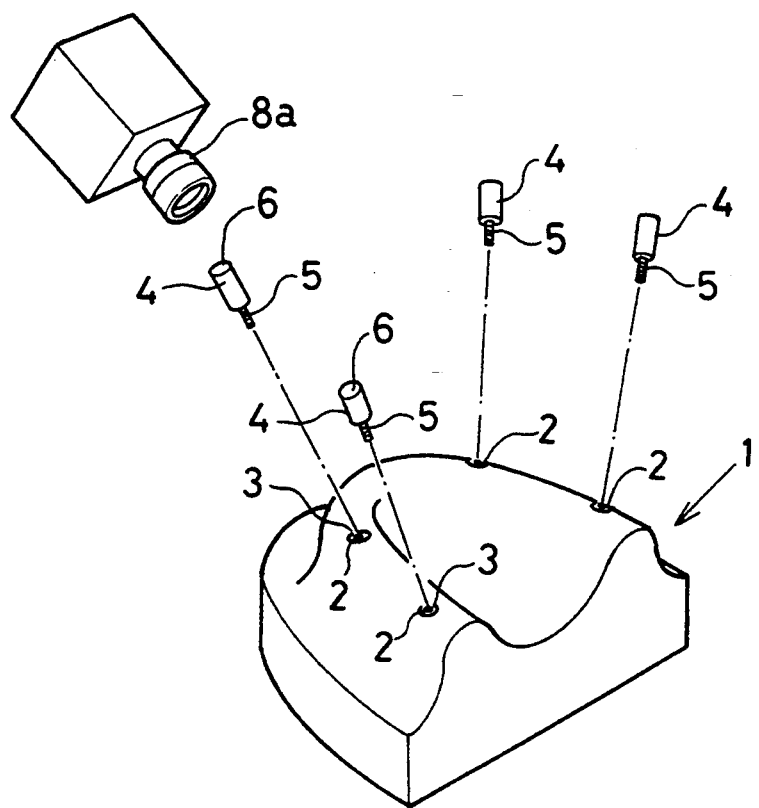
FIG. 4 is an explanatory view of a spacer which is attached to the implant structure according to the first embodiment of the invention.

FIG. 1 illustrates a measurement device for an implant structure according to a first embodiment of the invention. The measurement device measures the direction and positional relationship of bonding portions of the implant structure which is attached to a patient's jaw 1. FIGS. 2 through 4 show how a plurality of bonding portions of the implant structure are measured on a monitor. In this instance, the patient's jaw, shown in FIGS. 1 through 4, is not a mold taken out of the patient's jaw, but a schematic view of the upper jaw or the lower jaw of the patient for the purpose of convenience.

The following discussion describes how a plurality of bonding portions on the implant structure are measured.

The process set forth herein is based on the assumption that the patient has no teeth as shown in FIG. 2.

A plurality of implant structures 2 are implanted in the jaw 1 as shown in FIG. 3. These implant structures 2 are individually embedded in the jaw 1. Each of the four implant structures 2 includes female thread portions 3 which are exposed in the patient's mouth as shown in FIG. 4. Each of the female thread portions 3 corresponds to a plurality of bonding portions through which a prosthesis is attached to the implant structures 2.

To each of the female thread portions 3, a spacer 4 is attached to measure the direction, positional relationship and occlusive plane of the female thread portions 3. The spacer 4 is in the form of a cylinder having a male thread 5 which is screwed to the female thread portions 3. On an upper end of the spacer 4, a measuring object 6 is provided to measure the bonding position and the occlusive plane. In this embodiment of the invention, measuring the position, the direction and the occlusive plane of each of the female thread portions 3 means to measure a center and an extending direction of the circular end of the spacer 4. In this instance, spacers prepared herein have different lengths, and appropriate spacers are selected so that the upper end of the spacer forms the occlusive plane when attached to the implant structures 2. It is also noted that instead of the male thread 5, an elongated stud may be provided which is entered to the female thread portion 3, and various modifications of the male thread 5 may be provided.

By using a measurement device 7, the positions of the bonding portions and the occlusive plane of the implant structures 2 are measured (see FIG. 1). The measurement device 7 for the implant structures 2 has two cameras 8a, 8b which concurrently photograph each spacer 4 in the patient's mouth. A monitor device 9 is provided to display images photographed by the two cameras 8a, 8b. An electronic circuit 10 is provided in the form of a computer to measure the bonding direction, the positions of the bonding portions and the occlusive plane of the implant structures 2. The electronic circuit 10 measures shape, position and positional relationship by means of an image processing circuit on the basis of the images displayed on the monitor device 9. The center and the extending direction of the upper end of the measuring object 6 is measured on the basis of the shape of the measuring object 6 so as to lead to the position and direction of the screw hole of the female thread portion 3.

With the use of the image processing circuit, the shape of the measuring object 6 is measured as follows:

(1) Each spacer 4 in the patient's mouth is photographed by the two cameras 8a, 8b.

Figure 5:
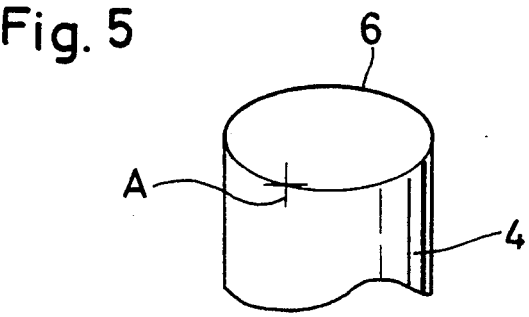
FIG. 5 an explanatory view of a measuring object which is subjected to an edge-find treatment according to the first embodiment of the invention.

(2) Since one edge of the measuring object 6 photographed by one camera 8a is displayed on the monitor device 9, the edge is specified by an electronic mouse to carry out an edge-find treatment as shown at A in FIG. 5. That is to say, the shape of the edge of the measuring object 6 is read by a read-out device 11 in the electronic circuit 10. In this instance, the shape of the measuring object 6 is in the form of an ellipse, and a part of the ellipse is specified by the electronic mouse.

(3) From the shape of the measuring object 6 which is subjected to the edge-find treatment, the computer of the electronic circuit 10 calculates the position and the direction of the screw hole of the female thread portion (bonding portion) 3 in a calculator device 12. The calculated position of the bonding portion in the implant structures 2 is stored in a memory circuit in the computer.

(4) Thereafter, the remaining edge of the measuring object 6 is processed with the edge-find treatment in the same manner as described above. Then the position and direction of the screw hole of the female thread portion 3 in each of the implant structures 2 are measured and stored in the computer. The upper end of the measuring object 6 photographed by the other camera 8b is specified by the electronic mouse so as to process the edge of the measuring object 6 with the edge-find treatment to read the shape of the edge of the measuring object 6. On the basis of the shape read by the read-out device 11, the computer of the electronic circuit 10 calculates the position and the screw hole direction of the female thread portion 3 and stores the results in the memory circuit. The remaining edge of the measuring object 6 is then processed with the edge-find treatment in the same manner as described above. The position and the screw hole direction of the female thread portion 3 in each of the implant structures 2 are measured and stored in the computer. Since the positional relationship of the two cameras 8a, 8b is predetermined, the positional relationship among the female thread portions 3 is measured in each of the implant structures 2. On the basis of the position of the measuring object 6, the occlusive plane is also measured. It is observed that instead of the edge-find treatment, the mark (A) may be scanned along the elliptical edge to relate the elliptical edge to the shape of the measuring object 6. It is also observed that a plurality of portions of the edge of the measuring object 6 may be specified by the electronic mouse so that the computer distinguishes the shape of the measuring object 6 on the basis of the positional relationship of the specified portions.

Figure 6:
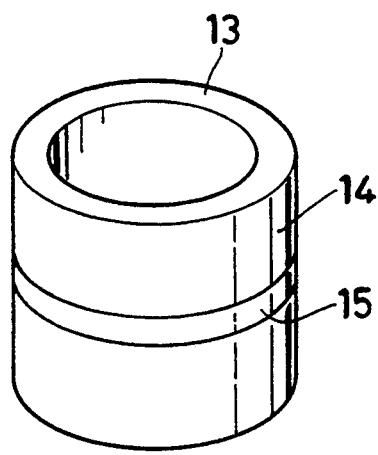
FIG. 6 is a perspective view of an auxiliary spacer according to the first embodiment of the invention.
Figure 7:
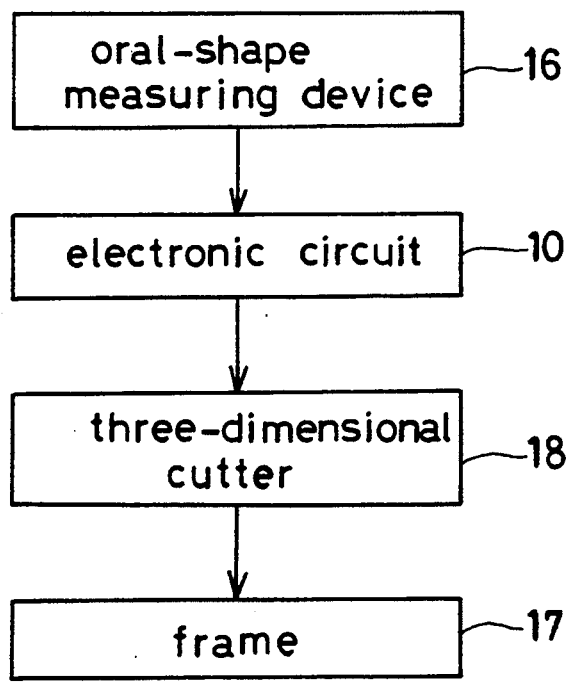
FIG. 7 is a schematic block diagram of a device in which a prosthesis is automatically milled on the basis of measurement results according to the first embodiment of the invention.

When it is difficult to photograph inside the patient's mouth, a cylindrical auxiliary spacer 14 is prepared, an upper end of which has a measurement object 13. The auxiliary spacer 14 is mounted on the spacer 4 as shown in FIG. 6. Then the mold of the patient's mouth is taken by means of an impression method. The auxiliary spacer 14 and the impression are then removed from the patient's mouth. By measuring the impression in which the shape of the measurement object 13 of each auxiliary spacer 14 is impressed, the position and the screw hole direction of the thread portion 3 are measured in addition to the occlusive plane. Groove 15 is provided on an outer surface of the auxiliary spacer 14 so as to improve the bonding with the impression.

Figure 8:
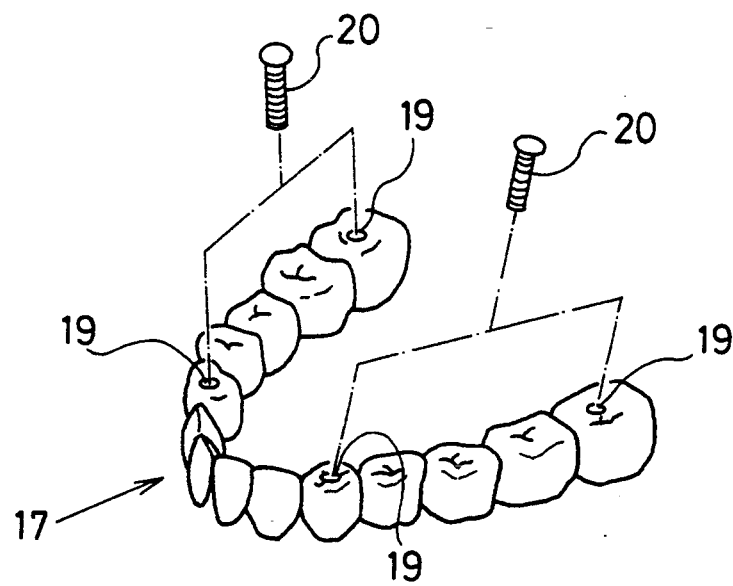
FIG. 8 is an explanatory view of a screw hole which is provided with the prosthesis according to the first embodiment of the invention.

One example of manufacturing the prosthesis is described as follows:

(1) A laser beam scanning is carried out in the patient's mouth in which a plurality of implant structures 2 are embedded with the use of an oral-shape measuring device 16. The measurement results are stored by the computer in the electronic circuit 10. On the basis of the values of the occlusive plane and the oral shape stored by the computer, a frame 17 is made of metal, ceramic material and synthetic resin which substantially forms a basic structure of the prosthesis. A reverse side of the frame 17, which is to be attached to the implant structure 2 is milled by a three-dimensional cutter 18 (CAD operation) to correspond the reverse side of the prosthesis to the oral shape of the patient. On the basis of the occlusive plane, the position and the screw hole direction of the female thread portion 3 each electronically stored in the electronic circuit 10, screw holes 19 are provided on the frame 17 corresponding to each female thread portion 3 of the implant structure 2 by using the three-dimensional cutter 18 as shown in FIG. 8. Each screw hole 19 serves as a throughhole through which a screw 20 is passed to attach the prosthesis to the implant structure 2. Artificial teeth are then arranged on the frame 17 by baking the ceramic material so as to provide the prosthesis. The prosthesis is attached to the patient's gingiva or the like according to the patient's needs.

According to the first embodiment of the invention, the spacer 4 is rigidly secured to the implant structure 2 without taking the molds several times. This makes it possible to precisely and quickly measure the position and the screw hole direction of the female thread portion 3 by directly measuring the measuring object 6 of the spacer 4. This substantially holds true when the auxiliary spacer 14 is used upon measuring the position and the screw hole direction of the female thread portion 3.

As opposed to the prior art in which numerous steps, intensive labor and skilled technicians are required to arrange the screw hole direction of the implant structure, it is possible to cure the teeth with less dental therapy cost because the necessity of the numerous mold processes is obviated. By precisely measuring the position and the screw hole direction of the female thread portion 3, it is possible to precisely drill a hole on the prosthesis so as to accurately bond the prosthesis to the bonding portions of the implant structure 2. This enables the protection of the implant structure against unfavorable stress so as to avoid inflammation at an interface between the implant structure and the human jaw. In addition, the necessity of providing an end play with the screw hole, thus preventing from microbes and foreign fouling matters being caught up between the implant structure and the patient's jaw is substantially eliminated. It is also possible to measure the occlusive plane so as to improve the manufacturing accuracy of the prosthesis by using the spacer 4.

Figure 9:
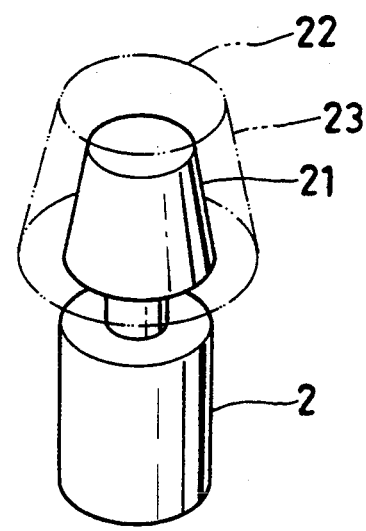
FIG. 9 is a perspective view of an implant structure made integral with a pedestal according to a second embodiment of the invention.

FIG. 9 shows the implant structure 2 in which a pedestal (bonding portion) 21 is made integral with the implant structure 2 according to a second embodiment of the invention. In this embodiment of the invention, a cup-shaped spacer 23 is provided, an upper end of which has a measuring object 22. The cup-shaped spacer 23 covers the pedestal 21. In this instance, there are provided a number of spacers of different lengths. The appropriate length of the spacer is selected taking the occlusive plane into consideration when the cup-shaped spacer 23 is placed on the pedestal 21. By measuring the measuring object 22 of the spacer 23, the position, direction of each pedestal 21 and the occlusive plane are determined.

Figure 10:
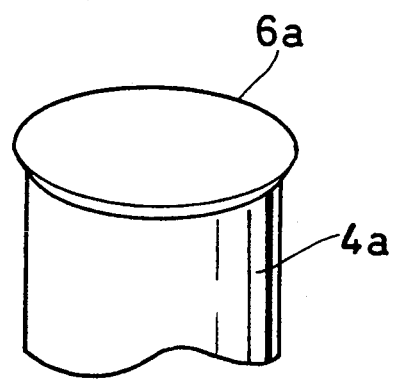
FIG. 10 is a perspective view of a measuring object of a spacer according to a third embodiment of the invention.

FIG. 10 shows a perspective view of a measuring object 6a of a spacer 4a according to a third embodiment of the invention. In this embodiment of the invention, an edge of the measuring object 6a is sharpened to positively carry out the edge-find treatment.

It is appreciated that the upper end of the measuring object 6 may be rectangular, triangular or polygonal. The upper end of the measuring object 6 may be concave or convex. Otherwise, three points or more may be specified on the upper end of the spacer so as to form a measuring object which has a shape provided by connecting the specified points.

It is noted that instead of using the cameras 8a, 8b, a laser type measuring device may be used to measure the positional relationship of the implant structure. The positional relationship of the measuring object may also be measured on the basis of the dimensions of the shape of the measuring object by using a single camera.

It is also noted that the position of the bonding portion may be determined by directly measuring the measuring object of the implant structure.

It is appreciated that the measuring object may be embedded in a living body, and it may be measured by using MRI image device, X-ray camera or the like so as to photograph the measuring object so that the position of the bonding portions of the implant structure may be measured on the basis of the measuring object embedded in the living body.

It is also observed that the measuring object includes a first portion which is embedded in the living body, and a second portion which is exposed in the mouth.

It is further noted that instead of the CCD camera, MRI image device or X-ray camera (CT scanner), a laser type measuring device may be used to photograph the shape inside the mouth by scanning the mouth.

It is appreciated that instead of discretely embedding the implant structure, the implant structure may be integrally embedded so that a plurality of the bonding portions may be measured.

It is also appreciated that the implant structure may be embedded in patient's gingiva to secure it to the jaw.

It is further noted that the cameras may be arranged to measure the positional relationship between the implant structure and the patient's teeth.

It is appreciated that instead of the flat occlusive plane, a curved occlusive plane may be measured by using the space or simulating it on the monitor display.

It is further appreciated that the position and direction of the measuring object may be directly read by photographs or films instead of reading it on the monitor display.

While the invention has been described with reference to the specific embodiments, it is understood that this description is not construed in a limiting sense in as much as various modifications and additions to the specific embodiments may be made by a skilled artisan without departing from the spirit and scope of the invention.

What is claimed is:

1. A measuring device comprising:
   implant structures adapted to be embedded into a patient's law, wherein said implant structures comprise bonding portions for securing a prosthesis to the implant structures;
   measuring objects provided on said bonding portions, respectively;
   a camera device which concurrently photographs specified shapes of said measuring objects; and a control device comprising:
   a read-out device which reads the specified shapes and a positional relationship of the measuring objects photographed by the camera device; and
   a calculator device which calculates a direction of each of the measuring objects based on the specified shapes read by the read-out device and which measures a positional relationship of the bonding portions based on the positional relationship of the measuring objects read by the read-out device.

2. The measuring device as recited in claim 1, wherein said camera device comprises two stereocameras which concurrently photograph the measuring objects.

3. The measuring device as recited in claim 1 or 2, wherein each of the measuring objects is attached to a spacer provided on corresponding bonding portions of said implant structures.

4. The measuring device as recited in claim 3, wherein the spacer is selected from selected spacers of different length, an upper end of the selected spacer forming an assumptive occlusive plane in a patient's mouth so that a real occlusive plane is determined by the control device based on the positional relationship of the measuring objects photographed by the camera device.

5. The measuring device as recited in claim 1, 2 or 4, wherein images photographed by the camera device are displayed on a monitor, and wherein the shape and positional relationship of the measuring objects are measured by said control device based on the images displayed on the monitor.

6. The measuring device as recited in claim 3, wherein images photographed by the camera are displayed on a monitor, and wherein the shape and the positional relationship of the measuring objects are measured by said control device based on the images displayed on the monitor.

7. The measuring device as recited in claim 2, wherein images photographed by the camera are displayed on a monitor, and wherein the shape and the positional relationship of the measuring objects are measured by said control device based on the images displayed on the monitor.

8. The measuring device as recited in claim 1, further comprising:
   an oral shape measuring device which measures an inside of a patient's mouth in which the implant structure is adapted to be embedded;
   a three-dimensional cutter which three-dimensionally mills a prosthesis;
   wherein the control device is adapted to control the three-dimensional cutter so as to correspond a shape of the prosthesis to a gingiva in the patient's mouth based on an oral shape measured by said oral shape measuring device.

9. The measuring device as recited in claim 1 or 8, wherein the control device controls the three-dimensional cutter to provide portions on the prosthesis which correspond to the bonding portions based on the direction and the position of the bonding portions determined by the calculator device.

10. A method of measuring a direction and positional relationship of bonding portions provided on implant structures, said method comprising the steps of:
    concurrently photographing specified shapes of measuring objects, provided on respective bonding portions of corresponding implant structures embedded in a human jaw, by means of a camera device;
    measuring the specified shapes and positional relationship of the measuring objects photographed by the camera device so as to determine the direction of each of the bonding portions based on the shapes of the measuring objects photographed by the camera device; and
    determining the positional relationship of the bonding portions based on the positional relationship of the measuring objects photographed by the camera device.

11. The method as recited in claim 1, further comprising the step of concurrently photographing the measuring objects using the camera device, said camera device further comprising two stereocameras.

12. The method as recited in claim 10 or 11, further comprising the step of attaching a spacer to corresponding bonding portions of said implant structures.

13. The method as recited in claim 12, further comprising the steps of selecting the spacer from spacers of different lengths, forming, with an upper end of the selected spacer, an assumptive occlusive plane in a patient's mouth, and determining a real occlusive plane based on the positional relationship of the measuring objects photographed by the camera.

14. The method as recited in claim 10, 11 or 13 further comprising the steps of displaying images photographed by the camera device on a monitor, and measuring the shape and the positional relationship of the measuring objects based on the images displayed on the monitor.

15. The method as recited in claim 12, further comprising the steps of displaying images photographed by the camera device on a monitor, and measuring the shape and the positional relationship of the measuring objects based on the images displayed on the monitor.

16. The method as recited in claim 11, further comprising the steps of displaying images photographed by the camera device on a monitor, and measuring the shape and the positional relationship of the measuring objects based on the images displayed on the monitor.

* * * * *